US005783395A

United States Patent [19]
Saito

[11] Patent Number: 5,783,395
[45] Date of Patent: Jul. 21, 1998

[54] OLIGONUCLEOTIDE FOR DETECTING STRIPE DISEASE RESISTANT RICES, AND A METHOD FOR USING THE OLIGONUCLEOTIDE TO DETECT STRIPE DISEASE RESISTANT RICES

[75] Inventor: Yuriko Saito, Hokkaido, Japan

[73] Assignee: General Manager of Hokkaido National Agricultural Equipment Station, Sapporo, Japan

[21] Appl. No.: 674,878

[22] Filed: Jul. 3, 1996

[30] Foreign Application Priority Data

Mar. 12, 1996 [JP] Japan .................................... 8-083207

[51] Int. Cl.$^6$ .............................. C12P 19/34; C12Q 1/68; C07H 21/04

[52] U.S. Cl. ................................. 435/6; 435/5; 435/91.2; 536/24.32; 536/24.33; 935/8; 935/77; 935/78

[58] Field of Search .................................. 935/77, 78, 8; 435/5, 6, 91.2; 536/24.32, 24.33

[56] References Cited

PUBLICATIONS

Kurata et. al. Nature Genetics 8:365–372 (Dec. 1994).
Hayakawa et. al. Proc. Natl. Acad. Sci USA 89:9865–9 (Oct. 1992).

Ivell et. al. Proc. Natl. Acad. Sci. USA 81:2006–10 (Apr. 1984).

Stewart, Jr. et. al. Biotechniques 14:748–751 (May 1993).

Linz. Methods in Molecular and Cellular Biology 2:98–102 (1991).

Sealy et. al. in Gel Electrophoresis of Nucleic Acids, edited by Rickwood et. al. IRL Press, New York (1990) pp. 51–70.

*Primary Examiner*—W. Gary Jones
*Assistant Examiner*—Debra Shoemaker
*Attorney, Agent, or Firm*—Nikaido, Marmelstein, Murray & Oram LLP

[57] ABSTRACT

There is provided an oligonucleotide for specifically detecting rice plants resistant to stripe disease, said oligonucleotide comprising a sort of nucleic acid sequence 5'-CAGACCGACC-3' SEQ ID NO: 1 and being capable of amplifying a specific DNA fragment of stripe disease resistant rice. There is also provided a method for specifically detecting rice plants resistant to stripe disease, said method comprising the steps of (1) isolating a genomic DNA from rice leaves; (2) amplifying a DNA fragment by polymerase chain reaction; (3) detecting stripe disease resistant rice plants by an agarose electrophoresis.

9 Claims, 1 Drawing Sheet

RESISTANT CULTIVARS SUSCEPTIBLE CULTIVARS 1 2 3 4 5 6 7 8 9 10 11 12 13 14 15 16

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 10 base pairs
( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO: 1:

CAGACCGACC 10

OLIGONUCLEOTIDE FOR DETECTING STRIPE DISEASE RESISTANT RICES, AND A METHOD FOR USING THE OLIGONUCLEOTIDE TO DETECT STRIPE DISEASE RESISTANT RICES

BACKGROUND OF THE INVENTION

This invention relates to an oligonucleotide for detecting stripe disease resistant rice, also relates to a method for using the oligonucleotide to detect stripe disease resistant rice.

Rice stripe disease occurs in Japan, China, Korea, Taiwan and Russia. An agent that causes rice stripe disease is RSV (rice stripe virus) which is transmitted by small brown planthoppers (*Laodelphax striatelluls Fallén*) in a persistent manner and passes through egg of an infective female to progeny. Infection of rice plant with RSV causes severe damage to agriculture.

To control stripe disease, rice cultivars with resistance to RSV have been bred in Japan. For breeding rice cultivars resistant to RSV, many plant materials generated after crossing a resistant plant with a susceptible one are inspected by inoculation testes. In the inoculation test, young seedlings of rice are inoculated with a colony of infective insects and are transplanted to a nursery box in an insect-free greenhouse. Within 2–3 weeks after inoculation, susceptible plants have symptoms of stripe disease and are discarded, whereas stripe disease resistant plants have no symptom and are selected for the next generation. However, this method is quite laborious and time-consuming, and requires a colony of infective insects and air-conditioned greenhouse. Especially, maintenance of the infecting ability of insects is very difficult, because the rate of infective individuals in a colony becomes lower than that in the former generation. For this reason, selection of infective individuals in a colony must be made by inoculation test or serological method every 5–7 generations.

SUMMARY OF THE INVENTION

An object of the present invention is to provide an oligonucleotide which can be effectively used to specifically detect stripe disease resistant rice, so that the detection of stripe disease resistant rice may be easily performed in a laboratory, dispensing with any laborious and time consuming operations.

Another object of the present invention is to provide a method of detecting stripe disease resistant rice with the use of the oligonucleotide, so that the detection of the resistant plants may be easily performed in a laboratory, dispensing with any laborious and time consuming operations.

According to the first aspect of the present invention, there is provided an oligonucleotide for specifically detecting stripe disease resistant rices, said oligonucleotide comprising a sort of nucleic acid sequence 5'-CAGACCGACC-3' SEQ ID NO. 1 and being capable of amplifying a specific DNA fragment of stripe disease resistant rice.

According to the second aspect of the present invention, there is provided a method for specifically detecting stripe disease resistant rices, said method comprising the steps of (1) isolating a genomic DNA from rice leaves; (2) amplifying a DNA fragment by polymerase chain reaction; (3) detecting stripe disease resistant rices by means of agarose gel electrophoresis.

The above objects and features of the present invention will become more understood from the following description with reference to the accompanying drawing.

BRIEF DESCRIPTIONON OF DRAWING(S)

FIG. 1 is a picture showing the bands of the amplified DNA fragments which were amplified in polymerase chain reaction and separated by agarose gel electrophoresis.

In FIG. 1, each lane shows a rice cultivar as follows.

1: Modan
2: St.No.1
3: Tsukinohikari
4: Akanezora
5: Koigokoro
6: Tochigi 2
7: Chugoku 31
8: Musashikogane
9: Akenohoshi
10: Norin 8
11: Nipponbare
12: Koshihikari
13: Koganebare
14: Tamakei 56
15: Hitomebore
16: DNA size marker

DETAILED DESCRIPTION OF THE PREFERRED EMBODIMENTS

Figure 1:
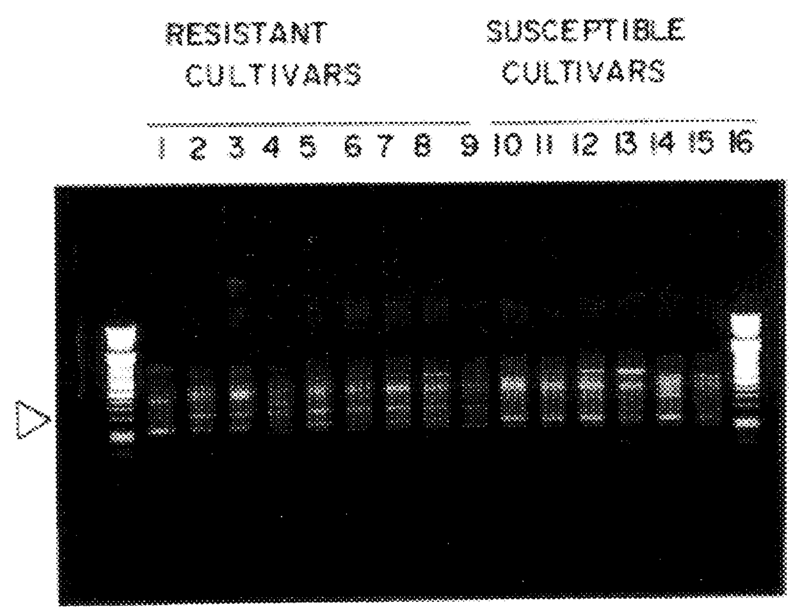

The following description will be given to explain about an oligonucleotide for detecting stripe disease resistant rice, and a method for using the oligonucleotide to detect stripe disease resistant rice.

According to the present invention, at first genomic DNA is isolated from young leaves of rice plants, then the oligonucleotide is used as a primer in PCR (polymerase chain reaction) during which DNA fragments are amplified. Afterwards, the amplified DNA fragments are separated by virtue of agarose gel electrophoresis, so as to detect stripe disease resistant rices by taking a photograph on agarose gel containing amplified separated DNA fragments.

Oligonucleotide is used as a primer in the PCR. Such Oligonucleotide comprises ten bases each having nucleic acid sequence 5'-CAGACCGACC-3'SEQ ID NO: 1, and can be synthesized in a method developed by R. T. Letsinger et al. (R. T. Letsinger, W. B. Lursford, J. Am. Chem. Society, 98, 3655), using a DNA synthesizer (Bechman System Plus). However, such oligonucleotide may also be synthesized in some other known methods.

The present invention will be described in detail below with reference to the following example, but it should be understood that the scope of the present application shall not be limited by such example.

EXAMPLE

<Isolation of Genomic DNA>

Genomic DNA was isolated from 3.0 g of young leaves from rice plants by CTAB (cetyl trimetyl ammounium bromide) method. Solutions a)–h) for use in CTAB method were prepared as follows. The prepared solutions of a),b), c),e),f),g) were autoclaved and then reserved at room temperature.

a) 2×CTAB Solution (2% CTAB, 0.1M Tris-HCl, pH 8.0, 1.4M NaCl

| | |
|---|---|
| CTAB (Sigma, USA) | 4 g |
| 1M Tris-HCl, pH 8.0 | 20 ml |
| 0.5M EDTA, pH 8.0 | 8 ml |
| 5M Sodium Chloride (NaCl) | 56 ml |

A necessary amount of distilled water ($dH_2O$) was used to mix with the above agents until the total volume of thus formed solution becomes 200 ml.

b) 1×CTAB Solution

2×CTAB solution a) was diluted with the same volume of $dH_2O$.

c) 10% CTAB Solution (10% CTAB; 0.7M NaCl)

2 g of CTAB was solved in 17 ml of $dH_2O$. The solution was adjusted to 20 ml after adding 2.8 ml of 5M NaCl.

d) Chloroform/isoamylalcohol (24:1, v/v)

| | |
|---|---|
| Chloroform | 240 ml |
| Isoamylalcohol | 10 ml |

The above agents were mixed and preserved at 4° C.

e) Precipitation Buffer (1% CTAB, 5 mM Tris-HCl, pH 8.0, 10 mM EDTA)

| | |
|---|---|
| CTAB | 1 g |
| 1M Tris-HCl, pH 8.0 | 5 ml |
| 0.5M EDTA, pH 8.0 | 2 ml |

A necessary amount of $dH_2O$ was used to mix with the above agents until the total volume of thus formed solution becomes 100 ml.

f) 1M NaCl—TE (1M NaCl, 10 mM Tris-HCl, pH 8.0, 1 mM EDTA)

| | |
|---|---|
| 5M NaCl | 20 ml |
| 1M Tris-HCl, pH 8.0 | 1 ml |
| 0.5M EDTA | 0.2 ml |

A necessary amount of $dH_2O$ was used to mix with the above agents until the total volume of thus formed solution becomes 100 ml.

g) TE Buffer (10 mM Tris-HCl, pH 8.0, 1 mM EDTA)

| | |
|---|---|
| 1M Tris-HCl, pH 8.0 | 10 ml |
| 0.5M EDTA, pH 8.0 | 2 ml |
| $dH_2O$ | 988 ml |

h) 10×Ribonuclease A (RNase A) (10 mg/ml)

1 μl of 10 mg/ml RNase was added to 1 ml of autoclaved $dH_2O$ and preserved at −20° C.

The leaves (3.0 g of fresh weight) were frozen in liquid Nitrogen ($N_2$) and powdered using a cold mortar and pestle in liquid $N_2$. The green powder was suspended sufficiently by spatula in 3 ml of 2×CTAB solution and 6 ml of 1×CTAB solution (60° C.) in 50 ml polypropylene centrifuge tube and incubated at 55° C. for 30 minutes, thus obtaining a suspension. 9 ml of chloroform/isoamylalcohol was added to the suspension and swung gently at horizontal position for 30 minutes at room temperature. The upper layer of the suspension was separated by centrifugation (2,800 r.p.m. for 15 minutes at room temperature, Himac (Hitachi Japan)) and transferred into new 50 ml tube. The lower layer was combined with 6 ml of 1×CTAB solution and swung gently for 20 minutes again. After treating by means of centrifugation in the same manner as above, both upper layers were combined, and 15 ml of chloroform/isoamylalcohol was added thereinto and swung gently for 20 minutes. The upper layer was separated by means of the centrifugation as above and was mixed with 1/10 volume of 10% CTAB solution by turning upside down without using vortex. The nucleic acids were precipitated by adding the same volume of precipitation buffer and by mixing gently and carefully. After standing for 30 minutes, the precipitate separated by the same centrifugation as above was resuspended in 5 ml of 5M NaCl—TE and incubated at 55° C. until it was resolved completely. Into the solution was added the same volume of isopropylalcohol and mixed gently and carefully. The mixture was centrifuged at 2,600 r.p.m. for 5 minutes at room temperature, while precipitate was washed with 3 ml of 70% ethanol, followed by centrifugation as above. Into the precipitate was added 500 μl of TE and incubated at 55° C. till it was resolved. This solution was found containing RNA and DNA, and then RNA was digested by incubation of the solution at 55° C. for 30 minutes with RNase at a concentration of 1 μg/ml, and the genomic DNA was obtained. The size and yield of the genomic DNA were checked by agarose gel electrophoresis and such genomic DNA was preserved at 4° C.

<Polymerase Chain Reaction (PCR)>

PCR reaction will be described as follows.

Taq polymerase reaction buffer was prepared which contains:

(Perkin Elmer, USA, attached with Taq polymerase)

| | |
|---|---|
| Tris-HCl, pH 8.0 | 10 mM |
| Potassium chloride (KCl) | 50 mM |
| Magnesium chloride ($MgCl_2$) | 1.5 mM |
| Gelatin | 0.001% (w/v) |

Then, the following agents were prepared:

| | |
|---|---|
| Taq polymerase (Perkin Elmer, USA) | 0.5 unit |
| dATP, dGTP, dCTP, dTTP mix (Pharamacia, USA) each | 150 μM |
| Oligonucleotide, as primer | 0.25 μM |
| Rice genomic DNA, as template | 25 ng |

Afterwards, the following agents were added together to make each PCR reaction mixture having a total volume of 25 μl.

| | |
|---|---|
| Taq polymerase reaction buffer (10 × conc.) | 2.5 μl |
| Taq polymerase (0.5 units/μl) | 1.0 μl |
| dATP, dGTP, dCTP, dTTP mix (each 150 μM) | 1.5 μl |
| Oligonucleotide (10 μM in 1/10 TE) | 0.6 μl |

The 1/10 TE is a diluted TE (10 mM Tris-HCl, 1 mM EDTA, pH 8.0) at 10 times with $dH_2O$ and autoclaved for sterilization. $dH_2O$ is a distilled water (Nacalai, Japan) filtrated through 0.2 μm filter and sterilized by autoclaving.

PCR reaction was conducted first at 94° C. for 4 minutes, then was continued for 45 cycles with each cycle being conducted for 1 minute at 94° C., 1 minute at 36° C. and 2 minutes at 72° C., respectively. Finally, the PCR reaction was conducted at 72° C. for 7 minutes. The entire process of the PCR reaction employed GeneAmp PCR system 9600 (Perkin Elmer), GeneAmp PCR system 2400 (Perkin Elmer), and program control system PC-700 (ASTEC, Japan).

During the above PCR reaction, rice genomic DNA fragments were amplified.

<Detection of Amplified DNA Fragments>

The DNA fragments amplified by PCR reaction were separated by a 1.4% (w/v) agarose gel electrophoresis using an electrophoresis apparatus called mupid (Cosmo-Bio, Japan). In detail, agarose (0.42 g) was melt in 30 ml of TAE buffer (40 mM Tris-Acetate, 1 mM EDTA, pH 8.0) to make a gel/plate having a size of 5.9 cm ×10.7 cm ×0.5 cm. 9 µl of a PCR reaction products was mixed with 2 µl of electrophoresis dye, and the mixture thus formed was used as a sample to be electrophoresed using the gel/plate at 100 volts for 30 minutes, so as to separate amplified DNA fragments. After electrophoresis, the gel/plate was soaked in 0.5 µg/ml of etidium bromide solution for 30 min to stain amplified DNA fragments.

<Taking a Photograph>

After staining, a photograph was taken on a slightly washed gel, through a red filter MC-Rl (KANKO, Japan) at 1/1 sec of shutter speed, and using iris diaphragm 8 under long-wave length ultraviolet on a transilluminator (Funakoshi, Japan). The Polaroid film type 667 and MP-4 LAND CAMERA (Polaroid, USA) were used. The results are shown in FIG. 1. In FIG. 1, each lane represents a cultivar as follows. An arrow on the left in FIG. 1 is used to indicate specifically amplified DNA band (ca. 730 bp) of stripe disease resistant cultivars. As shown in FIG. 1, lanes 1–9 each having one horizontal luminous band directed by the arrow, are determined as resistant cultivars. Also in FIG. 1, lanes 10–15 not having any horizontal luminous band directed by the arrow, are determined as susceptible cultivars. Lane 16 is a marker used to indicate DNA size.

Therefore, stripe disease resistant cultivars and stripe disease susceptible cultivars may easily determined with reference to FIG. 1.

(Resistant Cultivars)

1: Modan
2: St.No.1
3: Tsukinohikari
4: Akanezora
5: Koigokoro
6: Tochigi 2
7: Chugoku 31
8: Musashikogane
9: Akenohoshi (Susceptible Cultivars)

10: Norin 8
11: Nipponbare
12: Koshihikari
13: Koganebare
14: Tamakei 56
15: Hitomebore As is understood from the above description and examples, the use of the present invention permits easy detection of stripe disease resistant rices because such detection may be performed and completed in a laboratory. Therefore, it becomes possible to dispense with a large amount of labour and time which are otherwise unavoidable in a conventional method for detecting stripe disease resistance rices.

While the presently preferred embodiment of the this invention has been shown and described above, it is to be understood that the above disclosure is for the purpose of illustration and that various changes and modifications may be made without departing form the scope of the invention as set forth in the appended claims.

What is claimed is:

1. An oligonucleotide for specifically detecting stripe disease resistant rices, said oligonucleotide consisting of the nucleic acid sequence of SEQ ID NO: 1, wherein said oligonucleotide is suitable for specifically amplifying a DNA fragment of stripe disease resistant rice.

2. A method for specifically detecting stripe disease resistant rices, said method comprising the steps of:

(1) isolating a genomic DNA from rice leaves;

(2) amplifying DNA fragments from genomic DNA by polymerase chain reaction using an oligonucleotide for specifically detecting stripe disease resistant rices as a primer, said oligonucleotide consisting of the nucleic acid sequence of SEQ. ID NO: 1; and (3) detecting the presence of an amplified DNA fragment by means of agarose gel electrophoresis, wherein the presence of an amplified DNA fragments is indicative of a stripe disease resistant rice.

3. A method according to claim 2, wherein the genomic DNA is isolated from young leaves of rice plants, by means of CTAB (cetyl trimethyl ammonium bromide) method using CTAB solutions.

4. A method according to claim 3, wherein the young leaves of rice plants are processed into green powder which is in turn mixed with both 2×CTAB and 1×CTAB.

5. A method according to claim 2, wherein step (1) comprises centrifuging a solution containing the rice leaves and separating a top layer of the centrifugate thus produced from a lower layer, adding and mixing 1×CTAB into the lower layer, thereafter centrifuging the lower layer in a second centrifugation and separating a top layer of the centrifugate thus produced in the second centrifugation, thereafter combining the two top layers containing the genomic DNA together and then mixing the layers with a solution of chloroform/isoamylalcohol.

6. A method according to claim 2, wherein an oligonucleotide is used as primer in the step (2) for amplifying DNA fragments by polymerase chain reaction.

7. A method according to claim 2, wherein the polymerase chain reaction for amplifying DNA fragment is at first conducted at 94° C. for 4 minutes, then continued for 45 cycles with each cycle being conducted for 1 minute at 94° C., 1 minute at 36° C. and 2 minutes at 72° C. respectively, and finally conducted at 72° C. for 7 minutes.

8. A method according to claim 2, wherein in the step (3) for detecting stripe disease resistant rice plants, the DNA fragments amplified by polymerase chain reaction are separated by 1.4% (w/v) agarose gel electrophoresis.

9. A method according to claim 8, wherein an amount of polymerase chain reaction product is mixed with an electrophoresis dye and is electrophoresed using agarose gel at 100 volts for 30 min, so as to separate amplified DNA fragments.

* * * * *